(12) United States Patent
Liu et al.

(10) Patent No.: US 10,596,552 B2
(45) Date of Patent: Mar. 24, 2020

(54) CATALYST FOR PREPARING CUMENE AND USE THEREOF

(71) Applicants: CHINA PETROLEUM & CHEMICAL CORPORATION, Beijing (CN); Shanghai Research Institute of Petrochemical Technology, SINOPEC, Shanghai (CN)

(72) Inventors: Zhongneng Liu, Shanghai (CN); Xinghua Jiang, Shanghai (CN); Guoyao Gu, Shanghai (CN); Zejun Li, Shanghai (CN); Dongping Yuan, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 0 days.

(21) Appl. No.: 16/013,553

(22) Filed: Jun. 20, 2018

(65) Prior Publication Data
US 2018/0369788 A1 Dec. 27, 2018

(30) Foreign Application Priority Data

Jun. 21, 2017 (CN) .......................... 2017 1 0473465
Jun. 21, 2017 (CN) .......................... 2017 1 0473479
Jun. 21, 2017 (CN) .......................... 2017 1 0473492

(51) Int. Cl.
| | | |
|---|---|---|
| *B01J 23/652* | (2006.01) | |
| *B01J 35/00* | (2006.01) | |
| *C07C 5/03* | (2006.01) | |
| *B01J 23/58* | (2006.01) | |
| *B01J 21/04* | (2006.01) | |
| *B01J 32/00* | (2006.01) | |
| *C07C 15/085* | (2006.01) | |

(52) U.S. Cl.
CPC .......... *B01J 23/6525* (2013.01); *B01J 21/04* (2013.01); *B01J 23/58* (2013.01); *B01J 32/00* (2013.01); *B01J 35/002* (2013.01); *B01J 35/006* (2013.01); *B01J 35/0013* (2013.01); *C07C 5/03* (2013.01); *C07C 15/085* (2013.01); *C07C 2523/58* (2013.01); *C07C 2523/652* (2013.01)

(58) Field of Classification Search
CPC ........ B01J 23/6525; B01J 21/04; B01J 23/58; B01J 32/00; C07C 5/03; C07C 15/085; C07C 2523/58; C07C 2523/652
USPC .......................... 502/306, 313, 317, 328, 330
See application file for complete search history.

(56) References Cited

U.S. PATENT DOCUMENTS

| | | | | |
|---|---|---|---|---|
| 3,635,841 | A * | 1/1972 | Keith | B01J 21/04 502/333 |
| 3,646,235 | A | 2/1972 | Little et al. | |
| 4,104,317 | A * | 8/1978 | Antos | B01J 23/6567 208/139 |
| 5,179,056 | A * | 1/1993 | Bartley | B01J 23/44 502/170 |
| 5,347,046 | A * | 9/1994 | White | B01J 23/52 560/245 |
| 6,245,307 | B1 * | 6/2001 | Inui | B01D 53/9418 423/213.5 |
| 6,593,270 | B1 * | 7/2003 | Krause | B01J 21/08 423/335 |
| 7,381,854 | B2 | 6/2008 | Birkhoff et al. | |
| 2001/0056036 | A1 * | 12/2001 | Siqin | B01J 21/04 502/328 |
| 2010/0048925 | A1 * | 2/2010 | Yamamoto | C07D 301/19 549/529 |
| 2011/0054227 | A1 * | 3/2011 | Cheung | B01J 20/0207 585/16 |

FOREIGN PATENT DOCUMENTS

CN 10 3071487 * 5/2013 .............. B01J 23/63

* cited by examiner

*Primary Examiner* — Patricia L. Hailey
(74) *Attorney, Agent, or Firm* — Novick, Kim & Lee, PLLC; Allen Xue

(57) ABSTRACT

Provided is a catalyst for preparing cumene and use thereof. The catalyst provided includes a carrier and an active ingredient. The active ingredient includes: ingredient (1), which is palladium element; and ingredient (2), which is one or more selected from a group consisting of alkali metal elements, alkaline earth metals and molybdenum element. When the catalyst is used for preparing cumene by α-methyl styrene hydrogenation, AMS conversion rate is high, and a product cumene has high selectivity.

20 Claims, No Drawings

US 10,596,552 B2

CATALYST FOR PREPARING CUMENE AND USE THEREOF

CROSS-REFERENCE TO RELATED APPLICATIONS

This application claims priorities of the following applications: Chinese patent application 201710473492.X, entitled "Catalyst for preparing cumene and preparation method thereof" and filed on Jun. 21, 2017; Chinese patent application 201710473479.4, entitled "Cumene catalyst and preparation method thereof" and filed on Jun. 21, 2017; Chinese patent application 201710473465.2, entitled "Catalyst for preparing cumene by hydrogenation" and filed on Jun. 21, 2017. The entirety of the above applications is incorporated herein by reference.

FIELD OF THE INVENTION

The present disclosure relates to the technical field of a catalyst for preparing cumene. The present disclosure further relates to use of the catalyst and, in particular, to use of the catalyst in preparation of cumene by α-Methyl styrene hydrogenation.

BACKGROUND OF THE INVENTION

At present, cumene output in the world reaches nearly ten million tons, and more than 90% of the cumene are used to produce phenol and acetone. In this process, α-methyl styrene (AMS), a byproduct, is generated generally, and it is difficult to separate and remove AMS in subsequent refining procedures. However, AMS can be converted into raw material cumene by hydrogenation, and the raw material cumene can be used again in an oxidation procedure. By doing this, unit consumption of cumene can be reduced; a yield coefficient of phenol can be improved; and cost of raw materials can be saved. In this way, not only consumption of propylene and benzene raw materials can be reduced, but also technical and economic indexes of a device can be improved.

500 tons of AMS may be generated as a byproduct by a device for producing phenol/acetone with an annual output of 10000 tons, and devices for producing phenol/acetone used abroad all comprise an AMS hydrogenation unit. A traditional method of producing cumene by AMS hydrogenation is a slurry process, in which a Reney nickel catalyst is used, but the slurry process has defects such as complicated procedures, low selectivity of catalysts and a short usage cycle. The slurry process is gradually replaced by a fixed bed process. Performance of hydrogenation catalysts are very critical for the fixed bed process. There are many reports on catalysts for producing cumene by AMS hydrogenation. Saito studied experiments of catalytic hydrogenation to AMS using platinum as a catalyst. Phenolchemie Co. used $Cu_2Cr_2Ni$ to perform AMS hydrogenation. Chongheng He studied high-temperature thermal sintering of a palladium/alumina catalyst. Franco C et al. used a Pd/C catalyst in α-Methyl styrene hydrogenation. Little et al. respectively studied AMS selective hydrogenation properties of Ni, Pt, Pd, Co, $Cr_2O_3$ and several metal alloy catalysts. Activity and selectivity of non-palladium catalysts are not high, and catalysts which comprise palladium as a main or unique ingredient receive great attention in recent years. AMS is chemically active and has poor stability. Therefore, it is hoped that a hydrogenation catalyst has higher low-temperature activity and selectivity, as well as proper impurity-resistance property so as to increase a regeneration cycle of the catalyst, thereby prolonging the service life of the catalyst.

U.S. Pat. No. 3,646,235 discloses a use of nickel, platinum, palladium, cobalt, chromium oxides and mixed metal catalysts in AMS hydrogenation. Under conditions of a temperature of 24-50° C. and a pressure of 0.17-0.45 MPa, a Pd catalyst with metal content of 1-5% (by weight) is better.

Chinese patent CN1793089A discloses a method for selective hydrogenation of AMS to cumene by using a combined catalyst system having a nickel catalyst and a noble-metal catalyst. In the method, a combination of commercially available catalysts is packed, 70-95% of AMS conversion in a first reaction zone was achieved and at least 95% of AMS conversion in a second reaction zone was achieved.

There is a need for a novel catalyst used for production of cumene which has an improved AMS conversion rate and cumene selectivity.

SUMMARY OF THE INVENTION

The purpose of the present disclosure is to solve the technical problem of low AMS conversion rate and low cumene selectivity in preparation of cumene by AMS hydrogenation.

In a first aspect, the present disclosure provides a catalyst for preparing cumene, which comprises a carrier and an active ingredient. The active ingredient comprises:
ingredient (1), which is palladium element; and
ingredient (2), which is one or more selected from a group consisting of alkali metal elements, alkaline earth metal elements and molybdenum element.

According to the present disclosure, the palladium element can exist in the catalyst in a form of elementary substance, oxide, and/or salt.

According to the present disclosure, the alkali metal element can exist in the catalyst in a form of oxide and/or salt.

According to the present disclosure, the alkaline earth metal element can exist in the catalyst in a form of oxide and/or salt.

According to the present disclosure, the molybdenum element can exist in the catalyst in a form of oxide and/or salt.

It is founded unexpectedly by the inventors that ingredient (1) and ingredient (2) have a synergistic effect on improving the AMS conversion rate and the cumene selectivity.

According to the present disclosure, g/L can be used as a unit of measurement to describe content of ingredient (1) and ingredient (2), and it represents ingredient mass loaded in one liter of the carrier. A conversion relation between g/L and a commonly used mass percentage is as follows:

$g_{ingredient}/L_{carrier} = (g_{ingredient}/g_{carrier}) \times \rho_{carrier}$, wherein $\rho_{carrier}$ represents packing density of the carrier.

According to some preferred embodiments of the catalyst of the present disclosure, calculated by element, content of ingredient (1) is in a range of 0.01-10 g/L, preferably 0.05-5 g/L, and more preferably 0.1-4 g/L.

According to some preferred embodiments of the present disclosure, calculated by element, content of ingredient (2) is in a range larger than 0 g/L and equal to or less than 60 g/L, preferably 0.5-5 g/L, and more preferably 1.0-3.5 g/L.

According to the present disclosure, as a non-limitative example, content of ingredient (1) can be 0.1 g/L, 0.2 g/L, 0.5 g/L, 1 g/L, 1.5 g/L, 2 g/L, 2.7 g/L, 3 g/L, 3.5 g/L, 4 g/L, 4.5 g/L, 5 g/L, 5.5 g/L, 6 g/L, 6.5 g/L, 7 g/L, 8 g/L, 9 g/L and so on.

According to the present disclosure, as a non-limiting example, content of ingredient (2) can be 0.01 g/L, 0.06 g/L, 0.12 g/L, 0.15 g/L, 0.18 g/L, 0.24 g/L, 0.30 g/L, 0.5 g/L, 1.0 g/L, 2.0 g/L, 3.0 g/L, 4.0 g/L, 5.0 g/L, 10 g/L, 15 g/L, 20 g/L, 25 g/L, 30 g/L, 35 g/L, 40 g/L, 45 g/L, 50 g/L, 55 g/L and so on.

According to some preferred embodiments of the present disclosure, a mass ratio of ingredient (1) to ingredient (2) is in a range of (20-1):1, preferably (15-5):1, and more preferably (12-8):1.

According to some embodiments of the catalyst of the present disclosure, ingredient (2) is molybdenum element, an alkali metal element, or an alkaline earth metal element.

According to some preferred embodiments of the catalyst of the present disclosure, ingredient (2) comprises an alkali metal element and molybdenum element. Preferably, calculated by element mass, a mass ratio of the alkali metal element to the molybdenum element is in a range of (0.1-10):1, preferably (0.2-5):1, more preferably (0.25-4), and most preferably (1-4):1, such as 1:1, 1.5:1, 2:1, 3:1, or 4:1. In the presence of ingredient (1), the alkali metal element and molybdenum element have a synergistic effect on improving the AMS conversion rate and the cumene selectivity.

According to some preferred embodiments of the catalyst of the present disclosure, ingredient (2) comprises an alkaline earth metal element and molybdenum element. Preferably, calculated by element mass, a mass ratio of the alkali metal element to the molybdenum element is in a range of (0.1-10):1, preferably (0.2-5):1, more preferably (0.25-4), and further preferably (1-4):1, such as 1:1, 1.5:1, 2:1, 3:1, or 4:1. In the presence of ingredient (1), the alkaline earth metal element and molybdenum element have a synergistic effect on improving the AMS conversion rate and the cumene selectivity.

According to some preferred embodiments of the catalyst of the present disclosure, ingredient (2) comprises an alkali metal element, an alkaline earth metal element and molybdenum element. Preferably, calculated by element mass, a mass ratio of a sum of the alkali metal element and the alkali metal element to the molybdenum element is in a range of (0.1-10):1, preferably (0.2-5):1, more preferably (0.25-4), and further preferably (1-4):1, such as 1:1, 1.5:1, 2:1, 3:1, or 4:1. In the presence of ingredient (1), the alkali metal element, the alkaline earth metal element and molybdenum element have a synergistic effect on improving the AMS conversion rate and the cumene selectivity.

According to some examples of the present disclosure, ingredient (2) is one or more selected from a group consisting of the alkali metal elements and the alkaline earth metal elements, and the catalyst does not comprise a metal element selected from IVA group elements.

According to some embodiments of the present disclosure, the active ingredient consists of ingredient (1) and ingredient (2). That is, the catalyst does not contain any active ingredient other than ingredient (1) and ingredient (2).

According to some preferred embodiments of the catalyst of the present disclosure, the alkaline earth metal element is at least one selected from a group consisting of Ca, Mg, Sr and Ba.

According to some preferred embodiments of the catalyst of the present disclosure, the alkali metal element is at least one selected from a group consisting of Li, Na and K.

According to some preferred embodiments of the catalyst of the present disclosure, the carrier comprises at least one selected from a group consisting of alumina, zirconia, silica, titania and activated carbon. Preferably, the carrier comprises more than 80 wt %, preferably more than 90 wt %, and more preferably more than 95 wt % of alumina.

According to some preferred embodiments of the catalyst of the present disclosure, a BET specific surface area of the carrier is in a range of 60-200 $m^2/g$, preferably 80-150 $m^2/g$.

According to some preferred embodiments of the catalyst of the present disclosure, a pore volume of the carrier is in a range of 0.2-0.7 mL/g, preferably 0.3-0.5 mL/g.

According to some preferred embodiments of the catalyst of the present disclosure, the carrier has a most probable pore size in a range of 10-30 nm. It is found unexpectedly by the inventors of the present disclosure that the most probable pore size of the carrier affects diffusion performance of the catalyst. A proper most probable pore size can match with the molecular diameter of raw materials and the material viscosity, and thus improve diffusion performance of molecules of the raw materials, and is more favorable for the contact of the raw material molecules and an active center of the catalyst. Preferably, the most probable pore size of the carrier is in a range of 12-20 nm.

According to some preferred embodiments of the catalyst of the present disclosure, the alumina comprises δ-alumina, θ-alumina, or a mixture of the δ-alumina and the θ-alumina. Preferably, the alumina comprises more than 30 wt %, preferably more than 50 wt %, and more preferably more than 75 wt % of δ-alumina, θ-alumina, or a mixture of the δ-alumina and the θ-alumina. It is found unexpectedly by the inventors of the present disclosure that when the catalyst of the present disclosure using the mixture of the δ-alumina and the θ-alumina as the carrier is used in the preparation of cumene by α-methyl styrene hydrogenation, there is a synergistic effect on improving the AMS conversion rate and the cumene selectivity.

According to some preferred embodiments of the catalyst of the present disclosure, in the mixture of the δ-alumina and the θ-alumina, a mass ratio of the δ-alumina to θ-alumina is in a range of (0.2-5.0):1, preferably (0.45-3):1, and more preferably (0.5-2):1.

According to some preferred embodiments of the catalyst of the present disclosure, the palladium element is loaded in the carrier in a form of elementary substance. It is found by the inventors that when a size of palladium particles is too big, properties of bulk phase palladium are exhibited, which causes a lower activity in a hydrogenation reaction; and when the size of the palladium particles is too small, activity of the catalyst is overly high, which causes the catalyst to be less selective, and the activity of the catalyst decreases rapidly. It is found unexpectedly by the inventors that the catalyst has an optimum performance when the size of the palladium particles is in a range of 1.5-3 nm.

The catalyst provided by the present disclosure can be prepared by using a method known in the art, such as mixing, kneading, extruding, drying, calcinating of powders of the carrier, impregnating active ingredients, and drying, calcinating and activating the catalyst, and so on.

As an example, the catalyst of the present disclosure can be prepared using method, comprising:

step A, mixing a carrier with a solution of a compound containing an active ingredient;

step B, calcinating the carrier treated in step A, optionally drying the carrier treated in step A before calcinating, to obtain a catalyst precursor;

step C, mixing the catalyst precursor obtained in step B with a solution of a compound containing palladium element; and step D, calcinating the catalyst precursor treated in step C, optionally drying the catalyst precursor treated in step C before calcinating, to obtain the catalyst.

According to the present disclosure, the solution of a compound containing active ingredient is a solution of a compound containing ingredient (2), which is selected from a solution of a compound containing an alkali metal, a solution of a compound containing an alkaline earth metal, and a solution of a compound containing molybdenum element.

According to the present disclosure, there is no special limitation to the compound containing an alkali metal, the compound containing an alkaline earth metal, and the compound containing molybdenum element. As long as the compound containing an alkali metal, the compound containing an alkaline earth metal, and the compound containing molybdenum element are soluble in water, they can be used in the present disclosure. Examples are nitrate, hydrochloride, and C1-C4 carboxylate (oxalate is excluded because it is poorly soluble in water).

According to the present disclosure, there is no limitation to the compound containing palladium element. As long as the compound containing palladium element is soluble in water, it can be used in the present disclosure. Examples are palladium chloride, palladium acetate, palladium nitrate, chloropalladate, ammonium chloropalladate, and soluble complex compounds of palladium.

According to the present disclosure, as long as a solvent can dissolve the compound, it can be used for the preparation of the catalyst. However, in order to be economical and environment-friendly, a preferably used solvent is water.

According to some embodiments of the present disclosure, in step C, a pH value of the solution of a compound containing palladium is in a range of 2.0-4.0.

In order to obtain a catalyst with better strength, it is better to perform drying before calcinating in step B and/or step D. According to some embodiments of the present disclosure, in step B, a time duration for drying is in a range of 2-6 hours, and a temperature for drying is in a range of 80-120° C. According to some embodiments of the present disclosure, in step D, a time duration for drying is in a range of 2-6 hours, and a temperature for drying is in a range of 80-120° C.

According to the present disclosure, there is no special limitation to the calcinating atmosphere, as long as a comparable technical effect can all be achieved. In order to be economical, air atmosphere is used. For the convenience of comparison, air atmosphere is used in the embodiment of the present disclosure. According to embodiment s of the present disclosure, in step B, a time duration for calcinating is in a range of 3-8 hours, and a temperature for calcinating is in a range of 400-600° C. According to examples of the present disclosure, in step D, a time duration for calcinating is in a range of 3-8 hours, and a temperature for calcinating is in a range of 400-600° C.

In the above catalyst, Pd can be reduced to elementary substance, which can be directly used in a reaction for the preparation of cumene by α-methyl styrene hydrogenation. In the above catalyst, Pd can also exist in a form of Pd oxide, which is convenient for storage and stable for transportation, but the Pd oxide needs to be activated with a reducing agent before use. The reducing agent for activation can be hydrogen or a material containing hydrogen. For the convenience of comparison, Pd in the catalyst in examples of the present disclosure all exist as Pd oxide, and the Pd oxide should be activated at a temperature of 50° C. in a hydrogen atmosphere under a pressure of 0.4 MPa for 4 hours before use.

In a second aspect, the present disclosure further provides use of the above catalyst in the preparation of cumene by hydrogenating α-methyl styrene.

In a third aspect, the present disclosure further provides a method for preparing cumene, comprising contacting a raw material containing α-methyl styrene and hydrogen with the above catalyst provided by the present disclosure for reaction to generate cumene.

According to some preferred embodiments of the method of the present disclosure, the method is performed in a single reactor or a reactor having two stages in series, and the reactor is preferably a fixed bed reactor.

According to some preferred embodiments of the method of the present disclosure, the reaction is performed under a pressure in a range of 0.2-3.0 MPa, preferably 0.25-1.5 MPa.

According to some preferred embodiments of the method of the present disclosure, the reaction is performed under a temperature in a range of 30-100° C., preferably 40-60° C.

According to some preferred embodiments of the method of the present disclosure, the reaction is performed with a ratio of liquid circulation in a range of 1.0-10.0, preferably 2.0-7.0. If the ratio of liquid circulation is overly low, the concentration of α-methyl styrene at an inlet of the reactor is too high. As a result, polymerization of α-methyl styrene is easily caused. Polymer generated may cover the catalyst surface, which causes performance of the catalyst to decrease. If the ratio of liquid circulation is overly high, an amount of raw material needed to be processed by the catalyst increases. As a result, a space velocity increases, and the retention time is shortened, which causes a conversion rate to be reduced.

According to some preferred embodiments of the method of the present disclosure, a volume space velocity of the raw material containing α-methyl styrene is in a range of 0.3-3.0 $h^{-1}$, preferably 0.8-1.5 $h^{-1}$, such as 0.8 $h^{-1}$, 0.9 $h^{-1}$, 1.0 $h^{-1}$, 1.1 $h^{-1}$, 1.2 $h^{-1}$, 1.3 $h^{-1}$, 1.4 $h^{-1}$, 1.5 $h^{-1}$ and so on.

According to some preferred embodiments of the method of the present disclosure, a molar ratio of hydrogen to α-methyl styrene is in a range of (0.5-8):1, preferably (1-5):1, and more preferably (1.1-3.5):1.

According to some preferred embodiments of the method of the present disclosure, calculated by weight, the raw material contains 1-25% of α-methyl styrene and 75-99% of a solvent. It is found by the inventors that an overly high concentration of α-methyl styrene in the raw materials may result in that α-methyl styrene polymerizes to generate α-methyl styrene oligomer or a polymer having a higher molecular weight. Preferably, the raw material contains 2-10% of α-methyl styrene and 90-98% of a solvent. The solvent is, preferably, an inert solvent, which can be selected from methylbenzene, ethylbenzene, xylene, cumene and so on.

According to some preferred embodiments of the method of the present disclosure, the raw material containing α-methyl styrene is from a device for producing phenol and acetone using cumene.

The catalyst provided in the present disclosure has higher activity and selectivity when it is used in the preparation of cumene by α-methyl styrene hydrogenation. When the catalyst used in the present disclosure is used in the preparation of cumeme, an AMS conversion rate can reach 99.97%, and cumeme selectivity can reach 99.60%, the effect of which is good.

DETAILED DESCRIPTION OF THE EMBODIMENTS

The present disclosure will be explained in detail with reference to the examples, but the present disclosure is not limited by the following examples.

Each carrier used in the following examples and comparative examples has a bar length of 2 mm to 8 mm, a diameter of 1.8 mm to 2.2 mm, and a packing density of 0.5 g/mL to 0.8 g/mL.

Most probable pore sizes of the carriers used in examples and comparative examples were determined by the nitrogen adsorption BET method.

Example 1A

1. Preparation of a Catalyst

1 L of cylindrical alumina carrier (which had a most probable pore size of 15.8 nm, a specific surface area of 125 m$^2$/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of calcium nitrate containing 0.30 g of Ca; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which has Pd content of 2.7 g/L and Ca content of 0.30 g/L was obtained. In the obtained catalyst, the Pd particle size was 2.2 nm, which was obtained by using a TEM (transmission electron microscopy) average mensuration method.

2. Evaluation of the Catalyst 40 ml of the above prepared catalyst was packed into a fixed bed reactor, and then the catalyst was activated for 4 hours at a temperature of 50° C. under a hydrogen atmosphere of 0.4 MPa. After that, a reaction was performed. Conditions for the reaction are as follows: a temperature for the reaction was 45° C.; a pressure for the reaction was 0.3 MPa; a molar ratio of hydrogen to AMS was 1.2; a liquid space velocity of the raw material (which includes 21% of AMS and 79% of cumene) of the reaction was 1.0 h$^{-1}$; and a time duration for the reaction was 72 hours.

For the convenience of comparison, compositions of the catalyst and evaluation results thereof are listed in Table 1.

Example 2A

1 L of cylindrical alumina carrier (which had a most probable pore size of 15.8 nm, a specific surface area of 125 m$^2$/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of ammonium molybdate containing 0.30 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L and Mo content of 0.30 g/L) was obtained. In the obtained catalyst, the Pd particle size was 2.2 nm, which was obtained by using a TEM (transmission electron microscopy) average mensuration method.

2. Evaluation of the Catalyst

The evaluation of the catalyst prepared above was the same as that in Example 1A.

For the convenience of comparison, compositions of the catalyst and evaluation results thereof are listed in Table 1.

Example 3A

1. Preparation of a Catalyst

1 L of cylindrical alumina carrier (which had a most probable pore size of 15.8 nm, a specific surface area of 125 m$^2$/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of calcium nitrate containing 0.24 g of Ca and ammonium molybdate containing 0.06 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, Ca content of 0.24 g/L and Mo content of 0.06 g/L) was obtained. In the obtained catalyst, the Pd particle size was 2.2 nm, which was obtained by using a TEM (transmission electron microscopy) average mensuration method.

2. Evaluation of the Catalyst

The evaluation of the catalyst prepared above was the same as that in Example 1A.

For the convenience of comparison, compositions of the catalyst and evaluation results thereof are listed in Table 1.

Example 4A

1. Preparation of a Catalyst

1 L of cylindrical alumina carrier (which had a most probable pore size of 15.8 nm, a specific surface area of 125 m$^2$/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of calcium nitrate containing 0.18 g of Ca and ammonium molybdate containing 0.12 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, Ca content of 0.18 g/L and Mo content of 0.12 g/L) was obtained. In the obtained catalyst, the Pd particle size was 2.2 nm, which was obtained by using a TEM (transmission electron microscopy) average mensuration method.

2. Evaluation of the Catalyst

The evaluation of the catalyst prepared above was the same as that in Example 1A.

For the convenience of comparison, compositions of the catalyst and evaluation results thereof are listed in Table 1.

Example 5A

1. Preparation of a Catalyst

1 L of cylindrical alumina carrier (which had a most probable pore size of 15.8 nm, a specific surface area of 125 m²/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of calcium nitrate containing 0.15 g of Ca and ammonium molybdate containing 0.15 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, Ca content of 0.15 g/L and Mo content of 0.15 g/L) was obtained. In the obtained catalyst, the Pd particle size was 2.2 nm, which was obtained by using a TEM (transmission electron microscopy) average mensuration method.

2. Evaluation of the Catalyst

The evaluation of the catalyst prepared above was the same as that in Example 1A.

For the convenience of comparison, compositions of the catalyst and evaluation results thereof are listed in Table 1.

Example 6A

1. Preparation of a Catalyst

1 L of cylindrical alumina carrier (which had a most probable pore size of 15.8 nm, a specific surface area of 125 m²/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of calcium nitrate containing 0.12 g of Ca and ammonium molybdate containing 0.18 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, Ca content of 0.12 g/L and Mo content of 0.18 g/L) was obtained. In the obtained catalyst, the Pd particle size was 2.2 nm, which was obtained by using a TEM (transmission electron microscopy) average mensuration method.

2. Evaluation of the Catalyst

The evaluation of the catalyst prepared above was the same as that in Example 1A.

For the convenience of comparison, compositions of the catalyst and evaluation results thereof are listed in Table 1.

Example 7A

1. Preparation of a Catalyst

1 L of cylindrical alumina carrier (which had a most probable pore size of 15.8 nm, a specific surface area of 125 m²/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of calcium nitrate containing 0.06 g of Ca and ammonium molybdate containing 0.24 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, Ca content of 0.06 g/L and Mo content of 0.24 g/L,) was obtained. In the obtained catalyst, the Pd particle size was 2.2 nm, which was obtained by using a TEM (transmission electron microscopy) average mensuration method.

2. Evaluation of the Catalyst

The evaluation of the catalyst prepared above was the same as that in Example 1A.

For the convenience of comparison, compositions of the catalyst and evaluation results thereof are listed in Table 1.

Example 8A

1. Preparation of a Catalyst

1 L of cylindrical titania carrier (which had a most probable pore size of 16.8 nm and a specific surface area of 85 m²/g) was mixed with 500 ml of an aqueous solution of calcium nitrate containing 0.18 g of Ca and ammonium molybdate containing 0.12 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, Ca content of 0.18 g/L and Mo content of 0.12 g/L) was obtained. In the obtained catalyst, the Pd particle size was 2.2 nm, which was obtained by using a TEM (transmission electron microscopy) average mensuration method.

2. Evaluation of the Catalyst

The evaluation of the catalyst prepared above was the same as that in Example 1A.

For the convenience of comparison, compositions of the catalyst and evaluation results thereof are listed in Table 1.

Example 9A

1. Preparation of a Catalyst

1 L of cylindrical silica carrier (which had a most probable pore size of 21.8 nm and a specific surface area of 185 m²/g) was mixed with 500 ml of an aqueous solution of calcium nitrate containing 0.18 g of Ca and ammonium molybdate containing 0.12 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, Ca content of 0.18 g/L and Mo content of 0.12 g/L) was obtained. In the obtained catalyst, the Pd particle size was 2.2 nm, which was obtained by using a TEM (transmission electron microscopy) average mensuration method.

2. Evaluation of the Catalyst

The evaluation of the catalyst prepared above was the same as that in Example 1A.

For the convenience of comparison, compositions of the catalyst and evaluation results thereof are listed in Table 1.

Comparative Example 1A

1. Preparation of a Catalyst

1 L of cylindrical alumina carrier (which had a most probable pore size of 15.8 nm, a specific surface area of 125 m²/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of palladium chloride containing 3.0 g of Pd which was adjusted to a pH value of 3.2 using hydrochloric acid; and then a mixture obtained was dried at a temperature of 80° C. for 4 hours and calcinated at a temperature of 450° C. for 4 hours, and a desired catalyst (which had Pd content of 3.00 g/L) was obtained. In the obtained catalyst, the Pd particle size was 3.5 nm, which was obtained by using a TEM (transmission electron microscopy) average mensuration method.

2. Evaluation of the Catalyst

The evaluation of the catalyst prepared above was the same as that in Example 1A.

For the convenience of comparison, compositions of the catalyst and evaluation results thereof are listed in Table 1.

Comparative Example 2A

1. Preparation of a Catalyst

1 L of cylindrical alumina carrier (which had a most probable pore size of 15.8 nm, a specific surface area of 125 m²/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of calcium nitrate containing 3.00 g of Ca; then a mixture obtained was dried at a temperature of 80° C. for 4 hours and calcinated at a temperature of 450° C. for 4 hours, and a desired catalyst (which had Ca content of 3.00 g/L) was obtained.

2. Evaluation of the Catalyst

The evaluation of the catalyst prepared above was the same as that in Example 1A.

For the convenience of comparison, compositions of the catalyst and evaluation results thereof are listed in Table 1.

Comparative Example 3A

1. Preparation of a Catalyst

1 L of cylindrical alumina carrier (which had a most probable pore size of 15.8 nm, a specific surface area of 125 m²/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of ammonium molybdate containing 3.00 g of Mo; then a mixture obtained was dried at a temperature of 80° C. for 4 hours and calcinated at a temperature of 450° C. for 4 hours, and a desired catalyst (which had Mo content of 3.00 g/L) was obtained.

2. Evaluation of the Catalyst

The evaluation of the catalyst prepared above was the same as that in Example 1A.

For the convenience of comparison, compositions of the catalyst and evaluation results thereof are listed in Table 1.

TABLE 1

Compositions of the catalyst and evaluation results thereof

| | Contents of active ingredient, g/L | | | | AMS conversion rate, % | Cumene Selectivity, % |
|---|---|---|---|---|---|---|
| | Pd | Ca | Mo | Carrier | | |
| Example 1A | 2.70 | 0.30 | — | alumina | 94.33 | 93.51 |
| Example 2A | 2.70 | — | 0.30 | alumina | 94.50 | 96.62 |
| Example 3A | 2.70 | 0.24 | 0.06 | alumina | 98.54 | 98.31 |
| Example 4A | 2.70 | 0.18 | 0.12 | alumina | 99.56 | 99.21 |
| Example 5A | 2.70 | 0.15 | 0.15 | alumina | 98.16 | 98.21 |
| Example 6A | 2.70 | 0.12 | 0.18 | alumina | 96.76 | 97.87 |
| Example 7A | 2.70 | 0.06 | 0.24 | alumina | 96.03 | 97.12 |
| Example 8A | 2.70 | 0.18 | 0.12 | titania | 90.34 | 91.67 |
| Example 9A | 2.70 | 0.18 | 0.12 | silica | 91.57 | 92.09 |
| Comparative Example 1A | 3.00 | — | — | alumina | 90.13 | 91.37 |
| Comparative Example 2A | — | 3.00 | — | alumina | 0 | 0 |
| Comparative Example 3A | — | — | 3.00 | alumina | 0 | 0 |

Example 1B

1. Preparation of a Catalyst

1 L of cylindrical alumina carrier (which had a most probable pore size of 15.8 nm, a specific surface area of 125 m²/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of potassium carbonate containing 0.30 g of K; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L and K content of 0.30 g/L) was obtained. In the obtained catalyst, the Pd particle size was 2.2 nm, which was obtained by using a TEM (transmission electron microscopy) average mensuration method.

2. Evaluation of the Catalyst 40 ml of the catalyst was packed into a fixed bed reactor, and then the catalyst was activated for 4 hours at a temperature of 50° C. under a hydrogen atmosphere of 0.4 MPa. After that, a reaction was performed. Conditions for the reaction were as follows: a temperature for the reaction was 45° C.; a pressure for the reaction was 0.3 MPa; a molar ratio of hydrogen to AMS was 1.2; a liquid space velocity of the raw material (which includes 21% of AMS and 79% of cumene) of the reaction was 1.0 h⁻¹; and a time duration for the reaction was 72 hours.

For the convenience of comparison, compositions of the catalyst and evaluation results thereof are listed in Table 2.

Example 2B

1. Preparation of a Catalyst

1 L of cylindrical alumina carrier (which had a most probable pore size of 15.8 nm, a specific surface area of 125 m²/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of ammonium molybdate containing 0.30 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L and Mo content of 0.30 g/L) was obtained. In the obtained catalyst, the Pd particle size was 2.2 nm, which was obtained by using a TEM (transmission electron microscopy) average mensuration method.

2. Evaluation of the Catalyst

The evaluation of the catalyst prepared above was the same as that in Example 1B.

For the convenience of comparison, compositions of the catalyst and evaluation results thereof are listed in Table 2.

Example 3B

1. Preparation of a Catalyst

1 L of cylindrical alumina carrier (which had a most probable pore size of 15.8 nm, a specific surface area of 125 m²/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of potassium carbonate containing 0.24 g of K and ammonium molybdate containing 0.06 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, K content of 0.24 g/L and Mo content of 0.06 g/L) was obtained. In the obtained catalyst, the Pd particle size was 2.2 nm, which was obtained by using a TEM (transmission electron microscopy) average mensuration method.

2. Evaluation of the Catalyst

The evaluation of the catalyst prepared above was the same as that in Example 1B.

For the convenience of comparison, compositions of the catalyst and evaluation results thereof are listed in Table 2.

Example 4B

1. Preparation of a Catalyst

1 L of cylindrical alumina carrier (which had a most probable pore size of 15.8 nm, a specific surface area of 125 m²/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of potassium carbonate containing 0.18 g of K and ammonium molybdate containing 0.12 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, K content of 0.18 g/L and Mo content of 0.12 g/L) was obtained. In the obtained catalyst, the Pd particle size was 2.2 nm, which was obtained by using a TEM (transmission electron microscopy) average mensuration method.

2. Evaluation of the Catalyst

The evaluation of the catalyst prepared above was the same as that in Example 1B.

For the convenience of comparison, compositions of the catalyst and evaluation results thereof are listed in Table 2.

Example 5B

1. Preparation of a Catalyst

1 L of cylindrical alumina carrier (which had a most probable pore size of 15.8 nm, a specific surface area of 125 m²/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of potassium carbonate containing 0.15 g of K and ammonium molybdate containing 0.15 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, K content of 0.15 g/L and Mo content of 0.15 g/L) was obtained. In the obtained catalyst, the Pd particle size was 2.2 nm, which was obtained by using a TEM (transmission electron microscopy) average mensuration method.

2. Evaluation of the Catalyst

The evaluation of the catalyst prepared above was the same as that in Example 1B.

For the convenience of comparison, compositions of the catalyst and evaluation results thereof are listed in Table 2.

Example 6B

1. Preparation of a Catalyst

1 L of cylindrical alumina carrier (which had a most probable pore size of 15.8 nm, a specific surface area of 125 m²/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of potassium carbonate containing 0.12 g of K and ammonium molybdate containing 0.18 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, K content of 0.12 g/L and Mo content of 0.18 g/L) was obtained. In the obtained catalyst, the Pd particle size was 2.2 nm, which was obtained by using a TEM (transmission electron microscopy) average mensuration method.

2. Evaluation of the Catalyst

The evaluation of the catalyst prepared above was the same as that in Example 1B.

For the convenience of comparison, compositions of the catalyst and evaluation results thereof are listed in Table 2.

Example 7B

1. Preparation of a Catalyst

1 L of cylindrical alumina carrier (which had a most probable pore size of 15.8 nm, a specific surface area of 125 m$^2$/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of potassium carbonate containing 0.06 g of K and ammonium molybdate containing 0.24 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, and K content of 0.06 g/L and Mo content of 0.24 g/L) was obtained. In the obtained catalyst, the Pd particle size was 2.2 nm, which was obtained by using a TEM (transmission electron microscopy) average mensuration method.

2. Evaluation of the Catalyst

The evaluation of the catalyst prepared above was the same as that in Example 1B.

For the convenience of comparison, compositions of the catalyst and evaluation results thereof are listed in Table 2.

Example 8B

1. Preparation of a Catalyst

1 L of cylindrical titania carrier (which had a most probable pore size of 16.8 nm, a specific surface area of 85 m$^2$/g) was mixed with 500 ml of an aqueous solution of potassium carbonate containing 0.18 g of K and ammonium molybdate containing 0.12 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, K content of 0.18 g/L and Mo content of 0.12 g/L) was obtained. In the obtained catalyst, the Pd particle size was 2.2 nm, which was obtained by using a TEM (transmission electron microscopy) average mensuration method.

2. Evaluation of the Catalyst

The evaluation of the catalyst prepared above was the same as that in Example 1B.

For the convenience of comparison, compositions of the catalyst and evaluation results thereof are listed in Table 2.

Example 9B

1. Preparation of a Catalyst

1 L of cylindrical silica carrier (which had a most probable pore size of 21.8 nm, a specific surface area of 185 m$^2$/g) was mixed with 500 ml of an aqueous solution of potassium carbonate containing 0.18 g of K and ammonium molybdate containing 0.12 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, K content of 0.18 g/L and Mo content of 0.12 g/L) was obtained. In the obtained catalyst, the Pd particle size was 2.2 nm, which was obtained by using a TEM (transmission electron microscopy) average mensuration method.

2. Evaluation of the Catalyst

The evaluation of the catalyst prepared above was the same as that in Example 1B.

For the convenience of comparison, compositions of the catalyst and evaluation results thereof are listed in Table 2.

Comparative Example 1B

1. Preparation of a Catalyst

1 L of cylindrical alumina carrier (which had a most probable pore size of 15.8 nm, a specific surface area of 125 m$^2$/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of palladium chloride containing 3.0 g of Pd which was adjusted to a pH value of 3.2 using hydrochloric acid; and then a mixture obtained was dried at a temperature of 80° C. for 4 hours and calcinated at a temperature of 450° C. for 4 hours, and a desired catalyst (which has Pd content of 3.00 g/L) was obtained. In the obtained catalyst, the Pd particle size was 3.5 nm, which was obtained by using a TEM (transmission electron microscopy) average mensuration method.

2. Evaluation of the Catalyst

The evaluation of the catalyst prepared above was the same as that in Example 1B.

For the convenience of comparison, compositions of the catalyst and evaluation results thereof are listed in Table 2.

Comparative Example 2B

1. Preparation of a Catalyst

1 L of cylindrical alumina carrier (which had a most probable pore size of 15.8 nm, a specific surface area of 125 m²/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of potassium carbonate containing 3.00 g of K; then a mixture obtained was dried at a temperature of 80° C. for 4 hours and calcinated at a temperature of 450° C. for 4 hours, and a desired catalyst (which had K content of 3.00 g/L) was obtained.

2. Evaluation of the Catalyst

The evaluation of the catalyst prepared above was the same as that in Example 1B.

For the convenience of comparison, compositions of the catalyst and evaluation results thereof are listed in Table 2.

Comparative Example 3B

1. Preparation of a Catalyst

1 L of cylindrical alumina carrier (which had a most probable pore size of 15.8 nm, a specific surface area of 125 m²/g, and a pore volume of 0.46 mL/g, and contained 75 wt % of δ-alumina and θ-alumina, wherein the mass ratio of δ-alumina and θ-alumina was 1:1, and the rest was other phases of alumina) was mixed with 500 ml of an aqueous solution of ammonium molybdate containing 3.00 g of Mo; then a mixture obtained was dried at a temperature of 80° C. for 4 hours and calcinated at a temperature of 450° C. for 4 hours, and a desired catalyst (which had Mo content of 3.00 g/L) was obtained.

2. Evaluation of the Catalyst

The evaluation of the catalyst prepared above was the same as that in Example 1B.

For the convenience of comparison, compositions of the catalyst and evaluation results thereof are listed in Table 2.

TABLE 2

Compositions of the catalyst and evaluation results thereof

| | Contents of active ingredient, g/L | | | | AMS conversion rate, % | Cumene Selectivity, % |
|---|---|---|---|---|---|---|
| | Pd | K | Mo | Carrier | | |
| Example 1B | 2.70 | 0.30 | — | alumina | 95.63 | 94.21 |
| Example 2B | 2.70 | — | 0.30 | alumina | 94.50 | 96.62 |
| Example 3B | 2.70 | 0.24 | 0.06 | alumina | 98.67 | 98.48 |
| Example 4B | 2.70 | 0.18 | 0.12 | alumina | 99.97 | 99.60 |
| Example 5B | 2.70 | 0.15 | 0.15 | alumina | 98.32 | 98.39 |
| Example 6B | 2.70 | 0.12 | 0.18 | alumina | 97.21 | 98.15 |
| Example 7B | 2.70 | 0.06 | 0.24 | alumina | 96.12 | 97.51 |
| Example 8B | 2.70 | 0.18 | 0.12 | titania | 91.24 | 92.32 |
| Example 9B | 2.70 | 0.18 | 0.12 | silica | 92.36 | 92.87 |
| Comparative Example 1B | 3.00 | — | — | alumina | 90.13 | 91.37 |
| Comparative Example 2B | — | 3.00 | — | alumina | 0 | 0 |
| Comparative Example 3B | — | — | 3.00 | alumina | 0 | 0 |

Example 1C

1. Preparation of a Catalyst

1 L of cylindrical alumina carrier (which included 52 wt % of δ-alumina and 48 wt % θ-alumina and had a most probable pore size of 15.3 nm) was mixed with 500 ml of an aqueous solution of potassium carbonate containing 0.18 g of K and ammonium molybdate containing 0.12 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, K content of 0.18 g/L and Mo content of 0.12 g/L) was obtained.

2. Evaluation of the Catalyst 40 ml of the catalyst was packed into a fixed bed reactor, and then the catalyst was activated for 4 hours at a temperature of 50° C. under a hydrogen atmosphere of 0.4 MPa. After that, a reaction was performed. Conditions for the reaction were as follows: a temperature for the reaction was 45° C.; a pressure for the reaction was 0.3 MPa; a molar ratio of hydrogen to AMS was 1.2; a liquid space velocity of the raw material of the reaction (which included 21% of AMS and 79% of cumene) was 1.0 h⁻¹; and a time duration for the reaction was 72 hours.

For the convenience of comparison, compositions of the catalyst and evaluation results thereof are listed in Table 3.

Example 2C

1. Preparation of a Catalyst

1 L of cylindrical alumina carrier (which included 100 wt % of δ-alumina and has a most probable pore size of 17.9 nm) was mixed with 500 ml of an aqueous solution of potassium carbonate containing 0.18 g of K and ammonium molybdate containing 0.12 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, K content of 0.18 g/L and Mo content of 0.12 g/L) was obtained.

2. Evaluation of the Catalyst

The evaluation of the catalyst prepared above was the same as that in Example 1C.

For the convenience of comparison, compositions of the catalyst and evaluation results thereof are listed in Table 3.

Example 3C

1. Preparation of a Catalyst

1 L of cylindrical alumina carrier (which included 100 wt % θ-alumina and had a most probable pore size of 18.4 nm) was mixed with 500 ml of an aqueous solution of potassium carbonate containing 0.18 g of K and ammonium molybdate containing 0.12 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, K content of 0.18 g/L and Mo content of 0.12 g/L) was obtained.

2. Evaluation of the Catalyst

The evaluation of the catalyst prepared above was the same as that in Example 1C.

For the convenience of comparison, compositions of the catalyst and evaluation results thereof are listed in Table 3.

Example 4C

1. Preparation of a Catalyst

1 L of cylindrical alumina carrier (which included 65 wt % of δ-alumina and 35 wt % θ-alumina and had a most probable pore size of 16.2 nm) was mixed with 500 ml of an aqueous solution of potassium carbonate containing 0.18 g of K and ammonium molybdate containing 0.12 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, K content of 0.18 g/L and Mo content of 0.12 g/L) was obtained.

2. Evaluation of the Catalyst

The evaluation of the catalyst prepared above was the same as that in Example 1C.

For the convenience of comparison, compositions of the catalyst and evaluation results thereof are listed in Table 3.

Example 5C

1. Preparation of a Catalyst

1 L of cylindrical alumina carrier (which included 35 wt % of δ-alumina and 65 wt % θ-alumina and had a most probable pore size of 15.8 nm) was mixed with 500 ml of an aqueous solution of potassium carbonate containing 0.18 g of K and ammonium molybdate containing 0.12 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, K content of 0.18 g/L and Mo content of 0.12 g/L) was obtained.

2. Evaluation of the Catalyst

The evaluation of the catalyst prepared above was the same as that in Example 1C.

For the convenience of comparison, compositions of the catalyst and evaluation results thereof are listed in Table 3.

Example 6C

1. Preparation of a Catalyst

1 L of cylindrical alumina carrier (which included 50 wt % of δ-alumina and 50 wt % θ-alumina and had a most probable pore size of 14.7 nm) was mixed with 500 ml of an aqueous solution of potassium carbonate containing 0.18 g of K and ammonium molybdate containing 0.12 g of Mo; then a mixture obtained was dried at a temperature of 80° C. for 4 hours and calcinated at a temperature of 450° C. for 4 hours; after that, a product obtained from calcination was mixed with 500 ml of an aqueous solution of palladium chloride containing 2.7 g of Pd which was adjusted to a pH value of 3.2 using hydrochloric acid; and at last, a mixture obtained was dried at a temperature of 80° C. for 4 hours and calcinated at a temperature of 450° C. for 4 hours, and a desired catalyst (which had Pd content of 2.7 g/L, K content of 0.18 g/L and Mo content of 0.12 g/L) was obtained.

2. Evaluation of the Catalyst

The evaluation of the catalyst prepared above was the same as that in Example 1C.

For the convenience of comparison, compositions of the catalyst and evaluation results thereof are listed in Table 3.

Comparative Example 1C

1. Preparation of a Catalyst

1 L of cylindrical alumina carrier (which included 100 wt % of γ-alumina and had a most probable pore size of 10.2 nm) was mixed with 500 ml of an aqueous solution of palladium chloride containing 2.7 g of Pd which was adjusted to a pH value of 3.2 using hydrochloric acid; and then a mixture obtained was dried at a temperature of 80° C. for 4 hours and calcinated at a temperature of 450° C. for 4 hours, and a desired catalyst (which had Pd content of 3.00 g/L) was obtained.

2. Evaluation of the Catalyst

The evaluation of the catalyst prepared above was the same as that in Example 1C.

For the convenience of comparison, compositions of the catalyst and evaluation results thereof are listed in Table 3.

Comparative Example 2C

1. Preparation of a Catalyst

1 L of cylindrical alumina carrier (which included 70 wt % of δ-alumina 30 wt % of γ-alumina and had a most probable pore size of 18.6 nm) were mixed with 500 ml of an aqueous solution of palladium chloride containing 3.00 g of Pd which was adjusted to a pH value of 3.2 using hydrochloric acid; and then a mixture obtained was dried at a temperature of 80° C. for 4 hours and calcinated at a temperature of 450° C. for 4 hours, and a desired catalyst (which had Pd content of 3.00 g/L) was obtained.

2. Evaluation of the Catalyst

The evaluation of the catalyst prepared above was the same as that in Example 1C.

For the convenience of comparison, compositions of the catalyst and evaluation results thereof are listed in Table 3.

Comparative Example 3C

1. Preparation of a Catalyst

1 L of cylindrical alumina carrier (which included 100 wt % of α-alumina and had a most probable pore size of 131.7 nm) was mixed with 500 ml of an aqueous solution of palladium chloride containing 3.00 g of Pd which was adjusted to a pH value of 3.2 using hydrochloric acid; and then a mixture obtained was dried at a temperature of 80° C. for 4 hours and calcinated at a temperature of 450° C. for 4 hours, and a desired catalyst (which had Pd content of 3.00 g/L) was obtained.

2. Evaluation of the Catalyst

The evaluation of the catalyst prepared above was the same as that in Example 1C.

For the convenience of comparison, compositions of the catalyst and evaluation results thereof are listed in Table 3.

TABLE 3

Phases and most probable pore sizes of the carriers
for the catalyst and evaluation results thereof

| | Phase of the carrier | Most probable pore size of the carrier, nm | AMS conversion rate, % | Cumene Selectivity, % |
|---|---|---|---|---|
| Example 1C | δ-alumina + θ-alumina | 15.3 | 99.97 | 99.60 |
| Example 2C | δ-alumina | 17.9 | 98.32 | 98.39 |
| Example 3C | θ-alumina | 18.4 | 97.21 | 98.15 |
| Example 4C | δ-alumina + θ-alumina | 16.2 | 99.86 | 99.74 |
| Example 5C | δ-alumina + θ-alumina | 15.8 | 99.36 | 99.15 |
| Example 6C | δ-alumina + θ-alumina | 14.7 | 99.14 | 99.24 |
| Comparative Example 1C | γ-alumina | 10.2 | 92.41 | 93.57 |
| Comparative Example 2C | δ-alumina + γ-alumina | 18.6 | 93.89 | 94.63 |
| Comparative Example 3C | α-alumina | 131.7 | 73.6 | 83.5 |

Although the present disclosure is described hereinabove by referring to some examples, various improvements can be made to the present disclosure, and components therein can be replaced by equivalents without departing from the scope of the present disclosure. In particular, as long as there is no conflict, all the technical features mentioned in all the examples disclosed in the present disclosure may be combined together in any manner, and the present disclosure does not provide exhaustive descriptions of these combinations just for saving space and resources. Therefore, the present disclosure is not limited by particular examples disclosed hereinabove, but includes all technical solutions that fall within the scope of the claims.

The invention claimed is:

1. A catalyst for preparing cumene, comprising a carrier and an active ingredient, wherein the active ingredient comprises:
   ingredient (1) that is palladium in elemental, salt, or oxide form, and
   ingredient (2) comprising molybdenum and, optionally, an alkali metal, an alkaline earth metal, or both, wherein ingredient (2) is in salt or oxide form,
   wherein, based on the weight of elemental metal, a content of palladium is 0.01-10 g/L and a mass ratio of ingredient (1) to ingredient (2) is in a range of (20-1):1, and wherein g/L is a unit representing a total mass of the active ingredient loaded on one liter of the carrier.

2. The catalyst according to claim 1, wherein a content of ingredient (2) is in a range larger than 0 g/L and equal to or less than 60 g/L.

3. The catalyst according to claim 2, wherein the content of ingredient (2) is 0.5-5 g/L.

4. The catalyst according to claim 3, wherein the content of ingredient (2) is 1.0-3.5 g/L.

5. The catalyst according to claim 1, wherein a mass ratio of ingredient (1) to ingredient (2) is (15-5):1.

6. The catalyst according to claim 5, wherein the mass ratio of ingredient (1) to ingredient (2) is (12-8):1.

7. The catalyst according to claim 1, wherein
   ingredient (2) comprises an alkali metal and molybdenum, wherein, based on the weight of elemental metal, a mass ratio of the alkali metal to molybdenum is in a range of (0.1-10):1;
   ingredient (2) comprises an alkaline earth metal and molybdenum; or
   ingredient (2) comprises an alkali metal element, an alkaline earth metal element and molybdenum.

8. A method for preparing cumene, which comprises contacting a raw material containing α-methyl styrene and hydrogen with the catalyst according to claim 7 for reaction to generate cumene.

9. The catalyst according to claim 1, wherein the alkaline earth metal element is at least one selected from the group consisting of Ca, Mg, Sr, and Ba, and the alkali metal element is at least one selected from the group consisting of Li, Na, and K.

10. The catalyst according to claim 1, wherein the carrier comprises at least one selected from the group consisting of alumina, zirconia, silica, titania, and activated carbon.

11. The catalyst according to claim 1, wherein the carrier has a BET specific surface area in a range of 60-200 m$^2$/g, a pore volume in a range of 0.2-0.7 mL/g, and a most probable pore size in a range of 10-30 nm.

12. The catalyst according to claim 10, wherein the alumina comprises δ-alumina, θ-alumina, or a mixture of the δ-alumina and the θ-alumina.

13. The catalyst according to claim 12, wherein in the mixture of δ-alumina and θ-alumina, a mass ratio of δ-alumina to θ-alumina is in a range of (0.2-5.0):1.

14. A method for preparing cumene, comprising contacting a raw material containing α-methyl styrene and hydrogen with the catalyst according to claim 1 to generate cumene.

15. The method according to claim 14, wherein the reaction is carried out under a pressure in a range of 0.2-3.0 MPa, at a temperature in a range of 30–100° C. at a ratio of liquid circulation of 1.0-10.0.

16. The method according to claim 14, wherein a volume space velocity of the raw material containing α-methyl styrene is in a range of 0.3-3.0 h$^{-1}$, and a molar ratio of hydrogen to α-methyl styrene is in a range of (0.5-8):1.

17. The method according to claim 14, wherein the raw material contains 1-25 wt % of α-methyl styrene and 75-99 wt % of a solvent.

18. The method according to claim 14, wherein the raw material containing α-methyl styrene is from a device for producing phenol and acetone using cumene.

19. The catalyst according to claim 1, wherein the content of ingredient (1) is 0.05-5 g/L.

20. The catalyst according to claim 1, wherein the content of ingredient (1) is 0.1-4 g/L.

* * * * *